United States Patent
Wakabayashi et al.

(10) Patent No.: US 9,737,459 B2
(45) Date of Patent: Aug. 22, 2017

(54) MEDICAL APPARATUS COMMUNICATION SYSTEM AND MEDICAL APPARATUS

(71) Applicant: NIHON KOHDEN CORPORATION, Tokyo (JP)

(72) Inventors: Tsutomu Wakabayashi, Tokyo (JP); Tatsuo Yoshida, Tokyo (JP); Naoto Akiyama, Tokyo (JP); Hiroyuki Satake, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 74 days.

(21) Appl. No.: 14/827,463

(22) Filed: Aug. 17, 2015

(65) Prior Publication Data

US 2016/0067141 A1 Mar. 10, 2016

(30) Foreign Application Priority Data

Sep. 4, 2014 (JP) ................................ 2014-180020

(51) Int. Cl.
| | | |
|---|---|---|
| *A61H 31/00* | (2006.01) | |
| *A61N 1/39* | (2006.01) | |
| *G09B 23/28* | (2006.01) | |

(52) U.S. Cl.
CPC ......... *A61H 31/007* (2013.01); *A61H 31/005* (2013.01); *A61N 1/3993* (2013.01);
(Continued)

(58) Field of Classification Search
CPC ............................ A61N 1/3993; A61H 31/005
(Continued)

(56) References Cited

U.S. PATENT DOCUMENTS

2004/0199212 A1* 10/2004 Fischell ................... A61N 1/08
607/32
2005/0131465 A1 6/2005 Freeman et al.
(Continued)

FOREIGN PATENT DOCUMENTS

EP 1697002 A1 9/2006
JP 2010-528722 A 8/2010
(Continued)

OTHER PUBLICATIONS

Extended European Search Report issued on Feb. 5, 2016, by the European Patent Office in counterpart European Application No. 15180844.1.

*Primary Examiner* — Kevin Kim
(74) *Attorney, Agent, or Firm* — Sughrue Mion, PLLC

(57) ABSTRACT

A medical apparatus communication system includes a first medical apparatus and a second medical apparatus. The first medical apparatus includes a first communicating unit which establishes a communication connection with the second medical apparatus to communicate with the second medical apparatus, and a first controlling unit which controls the first medical apparatus. The second medical apparatus includes a second communicating unit which establishes a communication connection with the first medical apparatus to communicate with the first medical apparatus, a second controlling unit which controls the second medical apparatus, and a second sound outputting unit which performs a sound output in accordance with a control of the second controlling unit. The second controlling unit controls the sound output of the second sound outputting unit in a predetermined timing after establishment of the communication connection between the first and second communicating units.

10 Claims, 3 Drawing Sheets

(52) U.S. Cl.
CPC ........ G09B 23/288 (2013.01); *A61H 2201/50* (2013.01); *A61H 2201/5043* (2013.01); *A61H 2201/5048* (2013.01); *A61H 2201/5058* (2013.01)

(58) Field of Classification Search
USPC .................................................... 340/539.12
See application file for complete search history.

(56) References Cited

U.S. PATENT DOCUMENTS

| | | |
|---|---|---|
| 2008/0300518 A1 | 12/2008 | Bowes |
| 2012/0123490 A1 | 5/2012 | Daynes et al. |
| 2012/0123504 A1 | 5/2012 | Daynes et al. |
| 2012/0226204 A1 | 9/2012 | Coleman et al. |
| 2013/0226049 A1 | 8/2013 | Kandori et al. |
| 2014/0358048 A1* | 12/2014 | Sullivan ............... A61N 1/3925 601/41 |

FOREIGN PATENT DOCUMENTS

| | | |
|---|---|---|
| JP | 2013-542814 A | 11/2013 |
| WO | 2012061322 A1 | 5/2012 |
| WO | 2012/073900 A1 | 6/2012 |

* cited by examiner

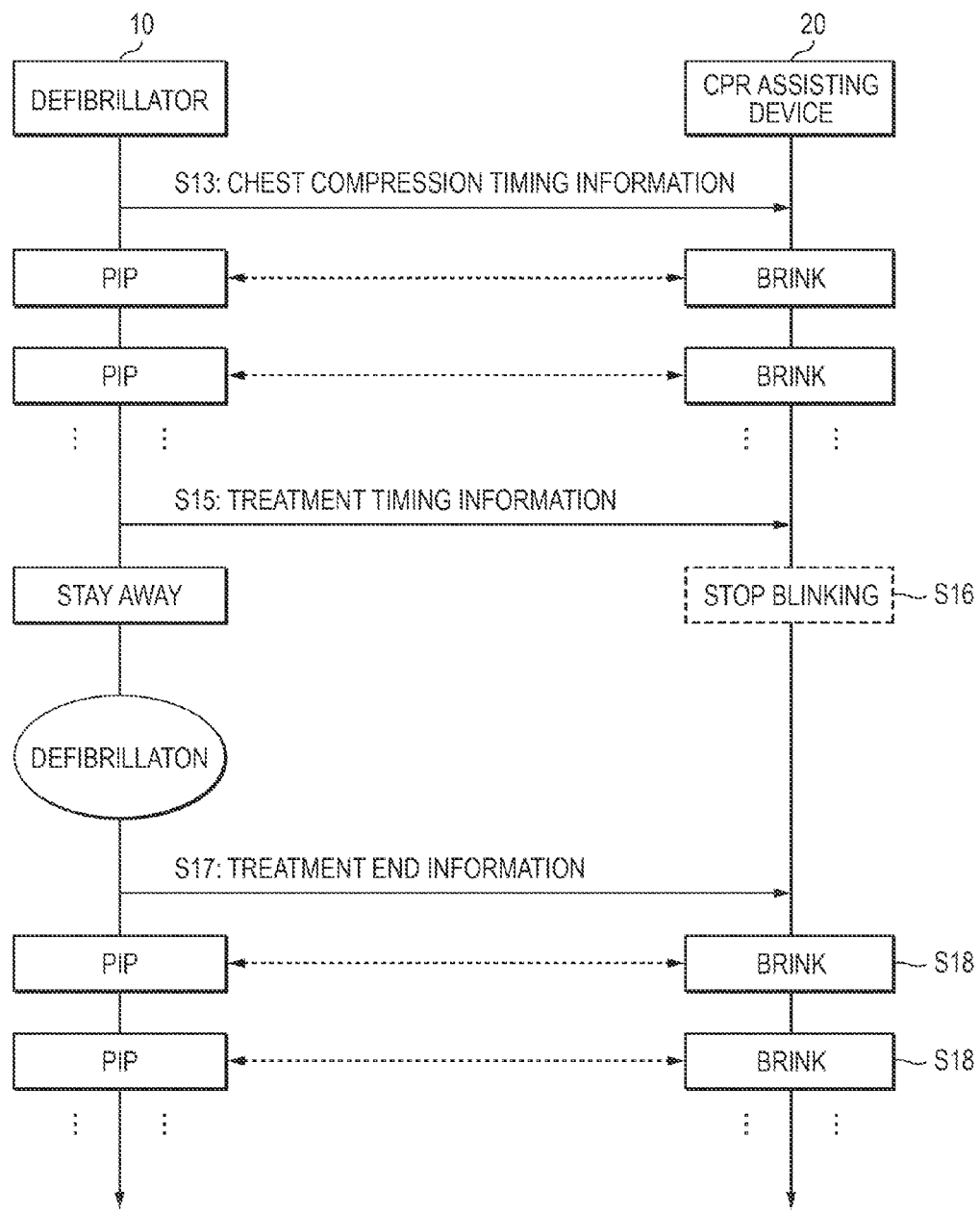

MEDICAL APPARATUS COMMUNICATION SYSTEM AND MEDICAL APPARATUS

CROSS-REFERENCE TO RELATED APPLICATION(S)

This Application is based upon and claims the benefit of priority from prior Japanese patent application No. 2014-180020, filed on Sep. 4, 2014, the entire contents of which are incorporated herein by reference.

BACKGROUND

The presently disclosed subject matter relates to a medical apparatus communication system, and also to a medical apparatus.

CPR (Cardio Pulmonary Resuscitation) is a technique which is essential in the field of the emergency medical service, and the life and death of the rescuee (patient) depend on the adequateness of the technique. When CPR is to be performed, the rescuer compresses the sternum which is in the upper side of the chest. Since CPR relates to the life and death of the rescuee, a device which is to be placed between the chest of the rescuee and the hands of the rescuer to assist the chest compression (hereinafter, such a device is referred to as a CPR assisting device) has been developed. In a CPR assisting device, it is detected whether an adequate force is applied at proper time intervals to the sternum or not, and, in accordance with the detection result, appropriate notification (such as "Insufficient compression depth" or "Compression timing is too late") is given to the rescuer.

Such a CPR assisting device has many occasions to be used concurrently with another medical apparatus such as an AED (Automated External Defibrillator) or a cardioverter defibrillator. When a CPR assisting device operates coordinately with a medical apparatus, it is possible to realize an adequate emergency procedure.

For example, JP-T-2013-542814 discloses a technique relating to communication among a plurality of defibrillators, and JP-T-2010-528722 discloses a technique relating to communication between a CPR assisting device and a defibrillator.

In a medical site or a scene of a medical training, it is supposed that many medical apparatuses are concurrently used. When a large-scale disaster (such as a high-rise building fire) occurs, for example, a case where many CPR assisting devices and AEDs (or cardioverter defibrillators) are simultaneously used may be caused. In a training session on CPR or the like, moreover, many CPR assisting devices and AEDs (or cardioverter defibrillators) are simultaneously used.

In the case where, in such a situation, medical apparatuses (for example, a CPR assisting device and an AED) operate while communicating with each other, the rescuer may be confused by voice guidance instructions output from the medical apparatuses.

The problem of the mixture of sound guidance instructions arises commonly not only in the case where a CPR assisting device and an AED operate coordinately with each other, but also in that where various kinds of medical apparatuses operate coordinately with one another.

SUMMARY

The presently disclosed subject matter may provide a medical apparatus communication system and medical apparatus in which, even in the case where a plurality of medical apparatuses are concurrently used, the user (rescuer) can perform a rescue procedure without confusion.

The medical apparatus communication system may include a first medical apparatus and a second medical apparatus. The first medical apparatus may include a first communicating unit which is configured to establish a communication connection with the second medical apparatus to communicate with the second medical apparatus, and a first controlling unit which is configured to control the first medical apparatus. The second medical apparatus may include a second communicating unit which is configured to establish a communication connection with the first medical apparatus to communicate with the first medical apparatus, a second controlling unit which is configured to control the second medical apparatus, and a second sound outputting unit which is configured to perform a sound output in accordance with a control of the second controlling unit. The second controlling unit may control the sound output of the second sound outputting unit in a predetermined timing after establishment of the communication connection between the first and second communicating units.

BRIEF DESCRIPTION OF THE DRAWINGS

FIG. 3 is a diagram showing another process flow of the defibrillator 10 and the CPR assisting device 20 in Embodiment 1.

DETAILED DESCRIPTION OF EXEMPLARY EMBODIMENTS

Embodiment 1

Figure 1:
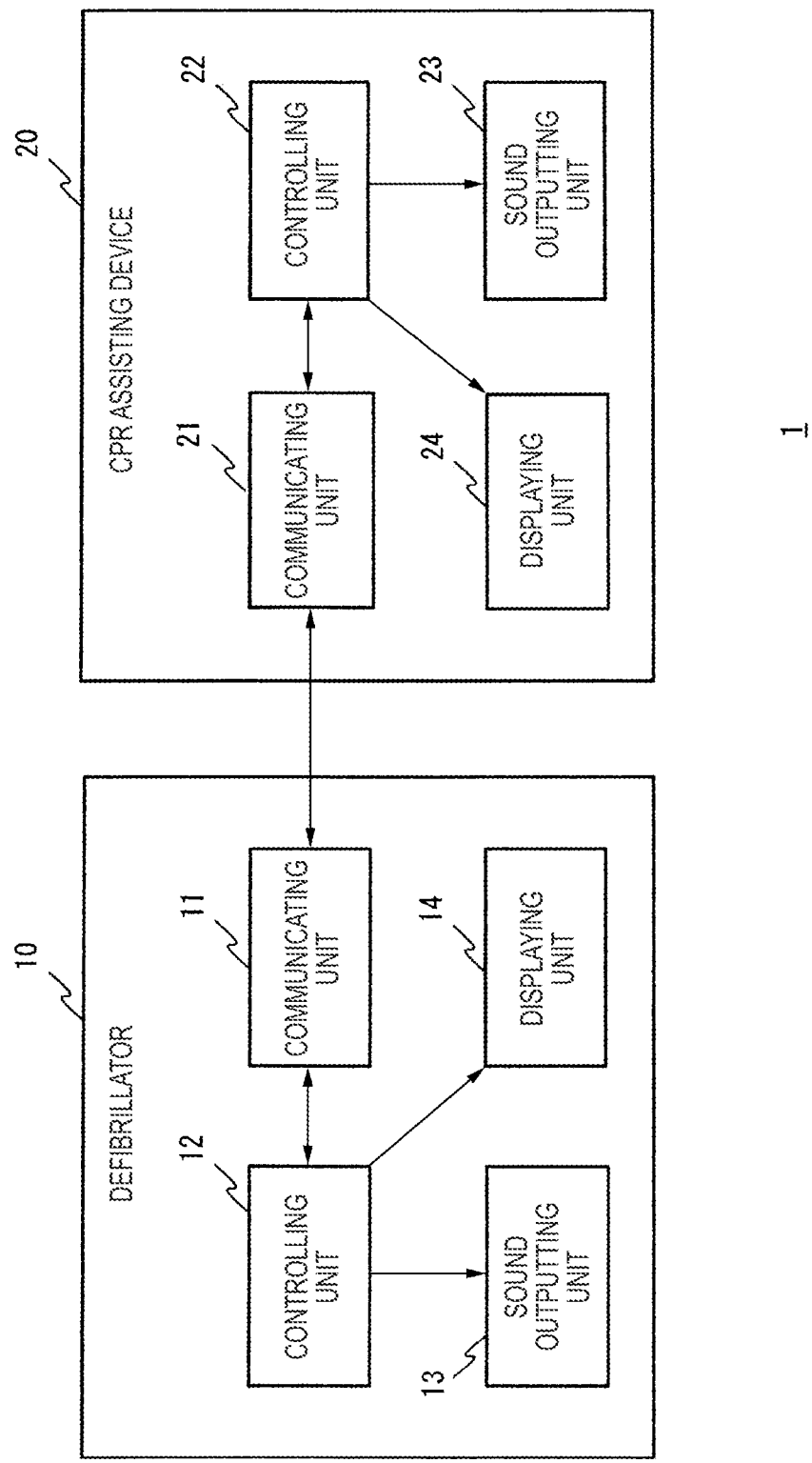
FIG. 1 is a block diagram of a medical apparatus communication system 1 of Embodiment 1.

Hereinafter, an embodiment of the presently disclosed subject matter will be described with reference to the drawings. FIG. 1 is a block diagram of a medical apparatus communication system 1 of Embodiment 1. The medical apparatus communication system 1 has a defibrillator 10 and a CPR (Cardio Pulmonary Resuscitation) assisting device 20. The defibrillator 10 and the CPR assisting device 20 are examples of a medical apparatus. Each of the defibrillator 10 and the CPR assisting device 20 is an apparatus which bidirectionally performs data communication.

The defibrillator 10 has a communicating unit 11, a controlling unit 12, a sound outputting unit 13, and a displaying unit 14. The CPR assisting device 20 includes a communicating unit 21, a controlling unit 22, a sound outputting unit 23, and a displaying unit 24. The defibrillator 10 further has an inputting unit (such as various buttons and knobs), storing unit (secondary storage device which stores various programs and sound data), and the like which are not shown. Similarly, the CPR assisting device 20 has also a storing unit (secondary storage device which stores various programs and sound data) and the like. The defibrillator 10 further includes electrodes which are to be contacted with the living body of the rescuee, a capacitor for charging, and the like.

Firstly, the operations of the components of the defibrillator 10 will be described. The communicating unit 11 establishes a communication connection with another medical apparatus (in the embodiment, the CPR assisting device 20), and transmits and receives data to and from the apparatus with which the communication connection is established. The communicating unit 11 may be a communication interface on which a short-range communication technique such as Bluetooth (registered trademark) is implemented.

The controlling unit 12 controls various operations of the defibrillator 10. The controlling unit 12 is realized by a CPU (Central Processing Unit) and various circuits (A/D converter and the like). The controlling unit 12 controls charge/discharge of energy for applying an electrical shock to the rescuee, the displaying operation of the displaying unit 14, and the like. In addition, the controlling unit 12 further controls the sound output from the sound outputting unit 13. In the following description, "sound" is a concept containing also a beep sound and other sounds in addition to so-called voice guidance instructions. The sound output control will be described later in detail with reference FIGS. 2 and 3.

For example, the sound outputting unit 13 is a speaker, and outputs an arbitrary sound in accordance with the operation of the defibrillator 10. For example, the sound outputting unit 13 outputs a sound such as "Charging," "Stay away," or "Restart chest compression." In the case where the chest compression is to be performed, the sound outputting unit 13 further outputs an ideal pace sound of the chest compression.

Under control of the controlling unit 12, the displaying unit 14 displays the operation state of the defibrillator 10, operation instructions to the user, and the like (performs a visual notification). The displaying unit 14 is configured by, for example, a liquid crystal display (LCD), various circuits for controlling the display, etc.

Next, the CPR assisting device 20 will be described. The CPR assisting device 20 is a device which is to be placed between the chest (preferably, just above the sternum) of the rescuee and the hands of the rescuer to assist the chest compression. The rescuee is a concept containing an injured or sick human (or alternatively referred to as a patient) and also a mannequin and the like. Namely, the CPR assisting device 20 may be used not only in a situation where the chest compression is actually performed, but also in the training of the chest compression. The CPR assisting device 20 has inside a sensor which is not shown. The sensor detects displacements which are caused when the compression is applied and released, and supplies a signal indicating such a displacement to the controlling unit 22.

The communicating unit 21 establishes a communication connection with another medical apparatus (in the embodiment, the defibrillator 10), and transmits and receives data to and from the apparatus with which the communication connection is established. Similarly with the communicating unit 11, the communicating unit 21 may be a communication interface on which a short-range communication technique such as Bluetooth (registered trademark) is implemented. For example, the establishment of the communication connection between the communicating units 21, 11 may be realized by pairing of Bluetooth (registered trademark) devices. In the communicating units 21, 11, after the communication connection is established, their time information is synchronized with each other. An arbitrary synchronization technique may be used in the synchronization.

The controlling unit 22 generally controls the CPR assisting device 20. The controlling unit 22 is realized by a CPU (Central Processing Unit) and various circuits. When the chest compression is performed, displacements are supplied from the above-described sensor to the controlling unit 22.

Based on the displacement detected by the above-described sensor, the controlling unit 22 detects the compression depth and rate of the chest compression which is applied to the rescuee. The controlling unit 22 reads out ideal compression depth and rate which are stored in the storing unit (not shown). The controlling unit 22 compares the read-out compression depth with the depth of the currently performed compression, and determines whether the current compression depth is adequate or not. Similarly, the controlling unit 22 compares the read-out compression rate with the rate of the currently performed compression, and determines whether the current compression rate is adequate or not.

For example, the techniques of the detection and determination of the compression depth and rate of the chest compression which are performed by the controlling unit 22 may be equivalent to those described in WO2012/073900.

The controlling unit 22 notifies whether the compression depth and rate are adequate or not, through the sound outputting unit 23. After the communication connection with the defibrillator 10 is established, however, the controlling unit 22 controls the sound output from the sound outputting unit 23 to be stopped in accordance with the state of the defibrillator 10. The sound output control will be described later with reference FIGS. 2 and 3.

Under the control of the controlling unit 22, the sound outputting unit 23 outputs guidance sounds. In accordance with the chest compression by using the CPR assisting device 20, for example, the sound outputting unit 23 outputs guidance sounds such as "Press more strongly," "Press more weakly," "Press more slowly," or "Press more quickly." After the communication connection with the defibrillator 10 is established as described above, however, the sound outputting unit 23 stops the sound output in accordance with the state of the defibrillator 10. This control will be described later in detail with reference FIGS. 2 and 3.

Under the control of the controlling unit 22, the displaying unit 24 visually informs of instructions and the like (performs a visual notification) to the user of the CPR assisting device 20. The displaying unit 24 is configured by, for example, a lamp, a small liquid crystal display, a circuit for controlling the lamp and the like, etc. For example, the displaying unit 24 causes the lamp to blink in synchronization with the most ideal pace of the chest compression. After the communication connection with the defibrillator 10 is established, a special control is applied to the display performed by the displaying unit 24. This control will be described later with reference FIGS. 2 and 3.

Figure 2:
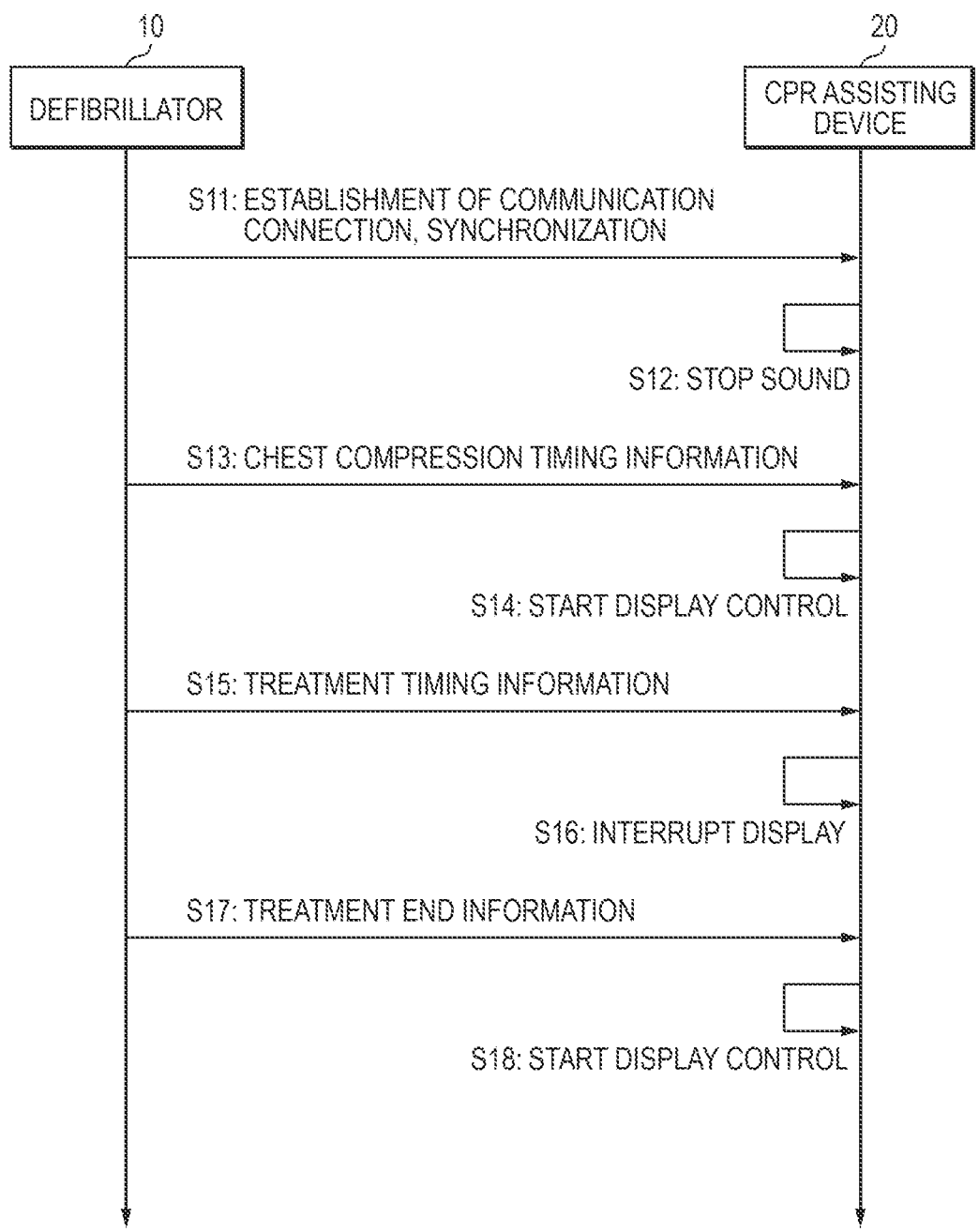
FIG. 2 is a diagram showing a process flow of a defibrillator 10 and a CPR assisting device 20 in Embodiment 1.

Referring to FIG. 2, the sound and display controls in the defibrillator 10 and the CPR assisting device 20 will be described. The communicating unit 11 of the defibrillator 10, and the communicating unit 21 of the CPR assisting device 20 establish the communication connection, and synchronize the time information (S11). After the communication connection is established, the controlling unit 22 of the CPR assisting device 20 stops the output of the guidance sound from the sound outputting unit 23 in accordance with the state of the defibrillator 10 (S12). In the case where the defibrillator 10 is in a state where the defibrillator 10 is connected to the rescuee through the electrodes, that where the defibrillator 10 has actually started the electrocardiogram analysis, or the like, for example, the operation of outputting the sound from the CPR assisting device 20 is stopped. The timing when the sound output from the CPR assisting device 20 (the predetermined state of the defibrillator 10) may be appropriately set by the rescuer. In the following description, it is assumed that, in the timing of S12, the defibrillator 10 and the rescuee are connected to each other through the electrodes, and therefore the sound output from the CPR assisting device 20 is stopped. The controlling unit 12 of the defibrillator 10 controls the sound outputting unit 13 so that, during the period when the sound output from the sound outputting unit 23 is stopped, the sound outputting unit 13 continues to be in the state where the sound output is enabled. Therefore, the sound outputting unit 13 continues to output the guidance sounds (sounds indicating the ideal pace of the chest compression).

The communicating unit 11 of the defibrillator 10 informs the CPR assisting device 20 of chest compression timing information indicating the ideal pace of the chest compression (S13). For example, the chest compression timing information includes information of "Pace sound of chest compression output every Z seconds from 13:XX:YY of Apr. 14, 2014." The format of the chest compression timing information is not limited to the above, and any format may be employed as far as the timing when the defibril for 10 outputs the sound is known. In accordance with the chest compression timing information, the controlling unit 22 of the CPR assisting device 20 controls the display on the displaying unit 24 (S14). For example, the lamp of the displaying unit 24 is caused to blink according to the information of the ideal chest compression pace.

The controlling unit 12 of the defibrillator 10 performs an analysis of an electrocardiogram of the rescuee, and the like. If the controlling unit 12 determines that defibrillation is to be performed, the communicating unit 11 informs the CPR assisting device 20 of treatment timing information (S15).

The communicating unit 21 of the CPR assisting device 20 receives the treatment timing information (S15). The treatment timing information is information indicating the timing when a treatment practice (in the embodiment, defibrillation) is to be performed. The treatment timing information is information which has a format that is approximately similar to that of the chest compression timing information, and which indicates, for example, "Electrocardiogram analysis for defibrillation is performed from 13:YY:ZZ of Apr. 14, 2014." In response to this, the controlling unit 22 interrupts the display (visual notification) on the displaying unit 24 (S16). For example, the controlling unit 22 interrupts the blinking of the lamp on the displaying unit 24.

The controlling unit 12 of the defibrillator 10 performs defibrillation. After defibrillation is performed, the communicating unit 11 of the defibrillator 10 transmits treatment end information to the CPR assisting device 20 (S17). The treatment end information (S17) informs not only of the performing of defibrillation, but also of the chest compression timing ("Pace sound of chest compression is output every Z seconds from 13:XX:YY of Apr. 14, 2014."). In response to this, the controlling unit 22 of the CPR assisting device 20 restarts the display on the displaying unit 24 (S18).

Next, a specific example of the sound outputs and displays of the defibrillator 10 and the CPR assisting device 20 will be described with reference to FIG. 3. In FIG. 3, the processes denoted by the same reference numerals as those in FIG. 2 are identical with the processes shown in FIG. 2, respectively.

The communicating unit 11 of the defibrillator 10 informs the CPR assisting device 20 of chest compression timing information indicating the ideal pace of the chest compression (S13). The controlling unit 12 of the defibrillator 10 controls the sound outputting unit 13 to output the sound of the ideal pace of chest compression. For example, the sound outputting unit 13 outputs sounds of "Pip," "Pip," "Pip."

The communicating unit 21 of the CPR assisting device 20 receives the chest compression timing information (S13). Then, the controlling unit 22 controls the displaying unit 24 to perform a display based on the chest compression timing information. The defibrillator 10 and the CPR assisting device 20 are time-synchronized with each other. In accordance with the chest compression timing information, the controlling unit 22 adjusts the display timing of the displaying unit 24 to be synchronized with the timing of outputting the sounds from the defibrillator 10. For example, the timings of outputting the sounds of "Pip," "Pip," "Pip" from the defibrillator 10 are substantially coincident with the lighting timings of the lamp on the case of the CPR assisting device 20.

The controlling unit 12 of the defibrillator 10 checks the electrocardiogram of the rescuee to determine whether defibrillation is to be performed on the rescuee or not. At this time, the controlling unit 12 causes the sound outputting unit 13 to output the guidance sound such as "Stay away." Then, the communicating unit 11 informs the CPR assisting device 20 of the treatment timing information (S15).

The communicating unit 21 of the CPR assisting device 20 receives the treatment timing information (S15). In order to enable the defibrillator 10 to start to check the electrocardiogram, the controlling unit 22 causes the display (for example, the blinking of the lamp) on the displaying unit 24 to be stopped (S16). In the case where the electrocardiogram is checked and the treatment is performed, namely, the displaying unit 24 does not perform a displaying operation such as the blinking of the lamp (S16).

In the case where, as a result of the analysis of the electrocardiogram, defibrillation is determined to be performed, energy is charged in the defibrillator 10, and, after the charging is ended, the defibrillator 10 performs defibrillation on the rescuee. After defibrillation is performed, the communicating unit 11 of the defibrillator 10 transmits the treatment end information (S17).

After the treatment end information is transmitted, the controlling unit 12 of the defibrillator 10 controls the sound outputting unit 13 to restart the output of the ideal pace of the chest compression. For example, the sound outputting unit 13 outputs sounds of "Pip," "Pip," "Pip."

The communicating unit 21 of the CPR assisting device 20 receives the treatment end information (S17). In accordance with the treatment end information, thereafter, the controlling unit 22 controls the displaying unit 24 to perform the display. The defibrillator 10 and the CPR assisting device 20 are time-synchronized with each other. Therefore, the timings of the sound output from the defibrillator 10 substantially coincide with that of the display on the CPR assisting device 20. For example, the timings of outputting the sounds of "Pip," "Pip," "Pip" from the defibrillator 10 are substantially coincident with the lighting timings of the lamp on the case of the CPR assisting device 20.

The process flows of FIGS. 2 and 3 are mere examples. The flows may be modified. For example, the process of stopping the sound output (S12), and that of notifying of the chest compression timing information (S13) may be reversed in order, or performed in a substantially same timing.

Next, effects of the medical apparatus communication system 1 of the embodiment will be described. After the communication connection between the defibrillator 10 and the CPR assisting device 20 is established, the sound output from the CPR assisting device 20 is stopped in accordance with the state of the defibrillator 10. Therefore, confusion due to the sound output from the CPR assisting device 20 can be avoided.

Also during the period when the sound output from the CPR assisting device 20 is stopped, the defibrillator 10 continues the sound output (for example, "Pip," "Pip" in FIG. 3). Since the sound output is performed only by the defibrillator 10, the rescuer can perform the treatment (in the embodiment, chest compression) without being confused, and while referring to the sound output. In the case where, as in the prior art, the defibrillator 10 and the CPR assisting device 20 operate without limiting both their sound outputs, there may arise a situation such as that where, despite that the defibrillator 10 outputs "Stay away," the CPR assisting device 20 outputs "Press more strongly the sternum." In the medical apparatus communication system 1 of the embodiment, only the defibrillator 10 performs the sound output, and therefore such a situation can be avoided.

Also during the period when the CPR assisting device 20 stops the sound output, the device continues the display (display of the pace of the chest compression) on the displaying unit 24. Therefore, the rescuer can visually know the ideal timing of the chest compression from the CPR assisting device 20 which is kept at the side of the rescuer.

The timing of the sound output from the defibrillator 10 is synchronized (performed in a substantially same timing) with that of the display on the CPR assisting device 20. In FIG. 3, for example, the timings of outputting the sounds of "Pip," "Pip" from the defibrillator 10 are substantially coincident with the timing of the blinking of the display on the CPR assisting device 20. Even in a situation where sound guidance and display guidance mixedly exist, therefore, the rescuer can perform the ideal chest compression without confusion.

In the case where the defibrillator 10 performs defibrillation, moreover, the CPR assisting device 20 stops the display guidance for promoting chest compression (S16 in FIGS. 2 and 3). In a timing when defibrillation may be performed, therefore, the display guidance for promoting chest compression can be stopped, and therefore chest compression can be safely performed.

After the defibrillation by the defibrillator 10 is ended, the CPR assisting device 20 restarts the display guidance for promoting chest compression (S17 and S18 in FIGS. 2 and 3). Therefore, the state where adequate chest compression can be performed is promptly attained after the defibrillation ended.

Although the invention conducted by the inventor has been specifically described based on the embodiment, the invention is not limited to the above-described embodiment, and it is a matter of course that various changes can be made without departing from the spirit of the invention.

In FIGS. 2 and 3, for example, it has been described that, after defibrillation is performed, the CPR. assisting device 20 restarts the displaying process (S18). The invention is not limited to this. In the case where the defibrillator 10 refers the electrocardiogram or the like of the rescuee and determines that the heart normally operates (if it is determined that the condition is improved), the defibrillator 10 may output a stop request for stopping the displaying process to the CPR assisting device 20. In accordance with the stop request, the controlling unit 22 of the CPR assisting device 20 stops the display by the displaying unit 24. According to the configuration, it is possible to avoid a situation such as that where, despite that the rescuee is rescued by defibrillation, the guidance for promoting chest compression is continued.

Hereinafter, correspondence relationships between the process units of the medical apparatus communication system set forth in the accompanying claims and the configuration shown in FIG. 1 will be schematically described. The first medical apparatus approximately corresponds to the defibrillator 10. The second medical apparatus approximately corresponds to the CPR assisting device 20. The first communicating unit approximately corresponds to the communicating unit 11. The first controlling unit approximately corresponds to the controlling unit 12. The first sound outputting unit approximately corresponds to the sound outputting unit 13. The second communicating unit approximately corresponds to the communicating unit 21. The second controlling unit approximately corresponds to the controlling unit 22. The second sound outputting unit approximately corresponds to the sound outputting unit 23. The second displaying unit approximately corresponds to the displaying unit 24.

In the above, it has been described that the CPR assisting device 20 stops the sound output according to the state of the defibrillator 10. Although the effects are reduced, even a configuration in which the volume of the sound output is lowered is sufficiently useful. Also such a configuration is an example of the invention. Namely, the CPR assisting device 20 is requested to control the sound output.

In the above description, after being connected to the defibrillator 10, the CPR assisting device 20 stops (controls) the sound output according to the state of the defibrillator 10. The invention is not limited to this. For example, the CPR assisting device 20 may stop (control) the sound output immediately after (or after elapse of a predetermined time period from) the connection with the defibrillator 10 is established. Namely, the CPR assisting device 20 is requested to stop (control) the sound output in a predetermined timing after the connection with the defibrillator 10 (for example, a timing when the defibrillator 10 is in a predetermined state, that after elapse of a predetermined time period from the timing when the defibrillator 10 is in a predetermined state, that immediately after establishment of the connection, or that after elapse of a predetermined time period from establishment of the connection).

The problem in that the user is confused by the mixture of sound guidance instructions may arise also in the case where medical apparatuses of another kind operate coordinately with one another. Therefore, the above-described operation of the medical apparatus communication system 1 (the operation of stopping a sound output of one of medical apparatuses) may be applied to another system in which arbitrary medical apparatuses operate coordinately with one another. It is a matter of course that, depending on the use or combination of medical apparatuses, there is a case where the sound of the CPR assisting device is preferentially output.

According to the presently disclosed subject matter, it is possible to provide a medical apparatus communication system and medical apparatus in which, even in the case where a plurality of medical apparatuses are concurrently used, the user (rescuer) can perform a rescue procedure without confusion.

What is claimed is:

1. A medical apparatus communication system including a first medical apparatus and a second medical apparatus, wherein
   the first medical apparatus includes a first communicating unit which is configured to establish a communication connection with the second medical apparatus to communicate with the second medical apparatus, first controlling unit which is configured to control the first medical apparatus, and a first sound outputting unit which is configured to perform a sound output in accordance with a control of the first controlling unit,
   the second medical apparatus includes a second communicating unit which is configured to establish a communication connection with the first medical apparatus to communicate with the first medical apparatus, a second controlling unit which is configured to control the second medical apparatus, and a second sound outputting unit which is configured to perform a sound output in accordance with a control of the second controlling unit, the second controlling unit controls the sound output of the second sound outputting unit in a predetermined timing after establishment of the communication connection between the first and second communicating units, and the first controlling unit controls the first sound outputting unit to enable the sound output during a period when the second sound outputting unit stops the sound output.

2. The medical apparatus communication system according to claim 1, wherein
the second medical apparatus further includes a second displaying unit which is configured to perform visual notification.

3. The medical apparatus communication system according to claim 2, wherein
time information of the first medical apparatus is synchronized with time information of the second medical apparatus.

4. The medical apparatus communication system according to claim 3, wherein
the first communicating unit informs the second communicating unit of chest compression timing information indicating an ideal pace of chest compression, the ideal pace being notified by the first sound outputting unit, and
the second controlling unit controls the second displaying unit to perform the visual notification based on the chest compression timing information which is informed to the second communicating unit.

5. The medical apparatus communication system according to claim 3, wherein
the first communicating unit informs the second communicating unit of treatment timing information indicating a timing when a predetermined treatment practice is to be performed, and,
based on the treatment timing information which is informed to the second communicating unit, the second controlling unit controls the second displaying unit to stop the visual notification during a period when the first medical apparatus performs the predetermined treatment practice.

6. The medical apparatus communication system according to claim 5, wherein,
after the first medical apparatus performs the predetermined treatment practice, the first communicating unit informs the second communicating unit of treatment end information, and,
based on the treatment end information which is informed to the second communicating unit, the second controlling unit controls the second displaying unit to restart the visual notification.

7. The medical apparatus communication system according to claim 5, wherein,
the first controlling unit determines whether a condition of a rescuee is improved by the predetermined treatment practice or not,
when the first controlling unit determines that the condition of the rescuee is improved, the first communicating unit transmits a stop request for stopping a displaying process to the second communicating unit, and,
in accordance with the stop request transmitted to the second communicating unit, the second controlling unit controls the second displaying unit to stop the visual notification.

8. The medical apparatus communication system according to claim 1, wherein
the first medical apparatus is a defibrillator which is configured to apply an electrical stimulus to a rescuee, and
the second medical apparatus is a CPR (Cardio Pulmonary Resuscitation) assisting device which is to be placed between a chest of the rescuee and hands of a rescuer to assist chest compression.

9. A medical apparatus which is configured to operate while communicating with another medical apparatus, comprising:
a communicating unit which is configured to establish a communication connection with the another medical apparatus to communicate with the another medical apparatus;
a controlling unit which is configured to control the medical apparatus; and
a sound outputting unit which is configured to perform a sound output in accordance with a control of the controlling unit, wherein
the controlling unit is configured to stop the sound output of the sound outputting unit or to lower volume of the sound output of the sound outputting unit in a predetermined timing after establishment of the communication connection with the another medical apparatus.

10. A medical apparatus which is configured to operate while communicating with another medical apparatus, comprising:
a communicating unit which is configured to establish a communication connection with the another medical apparatus to communicate with the another medical apparatus;
a controlling unit which is configured to control the medical apparatus; and
a sound outputting unit which is configured to perform a sound output, and,
when, after the communicating unit establishes the communication connection with the another medical apparatus, a sound output of the another medical apparatus is stopped, the controlling unit controls the sound outputting unit to enable the sound output.

* * * * *